US009747887B2

(12) United States Patent
O'Connell et al.

(10) Patent No.: US 9,747,887 B2
(45) Date of Patent: Aug. 29, 2017

(54) SYSTEMS AND METHODS OF ACTIVE NOISE REDUCTION IN HEADPHONES

(71) Applicant: BOSE CORPORATION, Framingham, MA (US)

(72) Inventors: Michael O'Connell, Northborough, MA (US); Ryan Termeulen, Watertown, MA (US); Daniel M. Gauger, Jr., Berlin, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 14/993,329

(22) Filed: Jan. 12, 2016

(65) Prior Publication Data

US 2017/0200444 A1 Jul. 13, 2017

(51) Int. Cl.

| | |
|---|---|
| ***G10K 11/16*** | (2006.01) |
| ***A61F 11/06*** | (2006.01) |
| ***H03B 29/00*** | (2006.01) |
| ***G10K 11/178*** | (2006.01) |
| ***H04R 1/10*** | (2006.01) |

(52) U.S. Cl.

CPC .......... *G10K 11/1782* (2013.01); *H04R 1/10* (2013.01); *G10K 2210/3027* (2013.01); *G10K 2210/3033* (2013.01); *G10K 2210/30232* (2013.01); *G10K 2210/504* (2013.01); *H04R 2460/01* (2013.01)

(58) Field of Classification Search

CPC ....... G10K 11/1782; G10K 2210/3027; G10K 2210/30232; G10K 2210/3033; G10K 2210/504; H04R 2460/01; H04R 1/10

USPC .......................................................... 381/71.6

See application file for complete search history.

(56) References Cited

U.S. PATENT DOCUMENTS

| | | | |
|---|---|---|---|
| 5,787,187 | A | 7/1998 | Bouchard et al. |
| 6,118,878 | A | 9/2000 | Jones |
| 6,697,299 | B2 | 2/2004 | Kato et al. |
| 7,529,379 | B2 | 5/2009 | Zurek et al. |
| 8,073,150 | B2 | 12/2011 | Joho et al. |
| 8,073,151 | B2 | 12/2011 | Joho et al. |

(Continued)

OTHER PUBLICATIONS

A. H. M. Akkermans, T. A. M. Kevenaar, D. W. E. Schobben, titled "Acoustic Ear Recognition for Personal Identification", (U.S.A), Fourth IEEE Workshop on Automatic Identification Advanced Technologies (AutoID'05)), 2005, p. 219-223.

(Continued)

*Primary Examiner* — Paul S Kim

(74) *Attorney, Agent, or Firm* — Lando & Anastasi, LLP

(57) ABSTRACT

Active noise reduction (ANR) headphones and associated methods are provided. The ANR headphones may include a memory to store a plurality of profiles each including controller information and acoustic parameters in addition to a profile selection routine executable by a processor of the ANR headphone. The profile selection routine may be configured to identify acoustic characteristics of a subject wearing the ANR headphone, compare the acoustic characteristics of the subject with the acoustic parameters of the plurality of profiles, select a profile from the plurality of profiles based on the comparison between the acoustic characteristics of the subject with the acoustic parameters of the selected profile, and provide the controller information of the selected profile to a noise reduction circuit of the ANR headphone.

24 Claims, 8 Drawing Sheets

(56) References Cited

U.S. PATENT DOCUMENTS

| | | | | |
|---|---|---|---|---|
| 8,085,946 | B2 | 12/2011 | Carreras et al. | |
| 8,090,114 | B2 | 1/2012 | Burge et al. | |
| 8,144,890 | B2 | 3/2012 | Carreras et al. | |
| 8,155,334 | B2 | 4/2012 | Joho et al. | |
| 8,165,313 | B2 | 4/2012 | Carreras | |
| 8,184,822 | B2 * | 5/2012 | Carreras | G10K 11/178 381/71.6 |
| 8,187,202 | B2 | 5/2012 | Akkermans et al. | |
| 8,208,650 | B2 | 6/2012 | Joho et al. | |
| 8,229,145 | B2 | 7/2012 | Coughlan et al. | |
| 8,280,066 | B2 | 10/2012 | Joho et al. | |
| 8,315,405 | B2 | 11/2012 | Bakalos et al. | |
| 8,345,888 | B2 | 1/2013 | Carreras et al. | |
| 8,355,513 | B2 | 1/2013 | Burge et al. | |
| 8,472,637 | B2 | 6/2013 | Carreras et al. | |
| 8,532,310 | B2 | 9/2013 | Gauger, Jr. et al. | |
| 8,611,553 | B2 | 12/2013 | Bakalos et al. | |
| 8,682,001 | B2 | 3/2014 | Annunziato et al. | |
| 8,798,283 | B2 | 8/2014 | Gauger, Jr. et al. | |
| 8,824,695 | B2 | 9/2014 | Bakalos et al. | |
| 9,047,855 | B2 | 6/2015 | Bakalos | |
| 2011/0002474 | A1 | 1/2011 | Fuller | |
| 2011/0007907 | A1 | 1/2011 | Park et al. | |
| 2011/0222700 | A1 | 9/2011 | Bhandari | |
| 2013/0322641 | A1 | 12/2013 | Carreras et al. | |
| 2014/0044275 | A1 * | 2/2014 | Goldstein et al. | H04R 3/002 381/71.6 |
| 2014/0363010 | A1 | 12/2014 | Christopher et al. | |
| 2015/0248879 | A1 | 9/2015 | Miskimen et al. | |

OTHER PUBLICATIONS

International Search Report and Written Opinion for application No. PCT/US2017/012854 dated Apr. 10, 2017.

* cited by examiner

SYSTEMS AND METHODS OF ACTIVE NOISE REDUCTION IN HEADPHONES

TECHNICAL FIELD

The technical field relates generally to systems and methods of active noise reduction (ANR) for headphones.

BACKGROUND

Noise reduction headphones typically block ambient noise from the subject's ear by generating noise canceling signals that destructively interfere with ambient sound to cancel it in the ear canal of the subject. These noise reduction devices generate the noise canceling signals based on an assumed set of acoustic characteristics of the subject's ear canal.

SUMMARY

According to one aspect, an active noise reduction (ANR) headphone is provided. The ANR headphone includes a speaker to receive a driver signal and generate sound based on the driver signal, a feedback microphone to detect sound proximate the speaker and generate a feedback audio signal, a memory to store a plurality of profiles, each profile including controller information and acoustic parameters, a noise reduction circuit coupled to the speaker and the feedback microphone, a processor coupled to the noise reduction circuit and the memory, and a profile selection routine executable by the processor. The profile execution routine may be configured to identify acoustic characteristics of a subject wearing the ANR headphone, compare the acoustic characteristics of the subject with the acoustic parameters of the plurality of profiles, select a profile from the plurality of profiles based on the comparison between the acoustic characteristics of the subject with the acoustic parameters of the selected profile, and provide the controller information of the selected profile to the noise reduction circuit.

In one example, the controller information may include information indicative of a relationship between at least the feedback audio signal and the driver signal. In this example, the noise reduction circuit may be configured to generate the driver signal based on at least the controller information of the selected profile and the feedback audio signal and provide the driver signal to the speaker.

In one example, the ANR headphone further includes a feed-forward microphone to detect ambient sound and generate a feed-forward audio signal and wherein the acoustic parameters in each profile include at least one of: a first energy ratio between the feedback audio signal and the feed-forward audio signal, a second energy ratio between the feedback audio signal and the driver signal, a first transfer function between the feedback audio signal and the feed-forward audio signal, or a second transfer function between the feedback audio signal and the driver signal.

In one example, the plurality of profiles includes a default profile and a customized profile and wherein the profile selection routine is further configured to determine whether the acoustic characteristics of the subject match the acoustic parameters of the customized profile. In this example, the profile selection routine may be further configured to select the profile at least in part by selecting the customized profile responsive to the acoustic characteristics of the subject matching the acoustic parameters of the customized profile and/or to select the profile at least in part by selecting the default profile responsive to the acoustic characteristics of the subject not matching the acoustic parameters of the customized profile. It is appreciated that the ANR headphone may further include a user interface coupled to the processor where the processor is further configured to provide an indication via the user interface that the default profile is selected.

In one example, the profile selection routine is further configured to select the profile with acoustic parameters that best fits the acoustic characteristics of the subject. In one example, the memory further stores a look-up table associating acoustic characteristics of the subject with the plurality of profiles and wherein the profile selection routine is further configured to select the profile with acoustic parameters that best fits the acoustic characteristics of the subject by the look-up table. In one example, the ANR headphone further includes an interface to receive a customized profile from an external entity and wherein the processor is further configured to store the customized profile in the memory.

In one example, the ANR headphone further includes a feed-forward microphone to detect ambient sound and generate a feed-forward audio signal and wherein the profiles further include at least one expected energy ratio between the feedback audio signal and the feed-forward audio signal and/or between the feedback audio signal and the driver signal. In this example, the profile selection routine may be further configured to determine at least one actual energy ratio between the feedback audio signal and the feed-forward audio signal and/or between the feedback audio signal and the driver signal. The profile selection routine may be further configured to compare a difference between the at least one expected energy ratio and the at least one of the actual energy ratio with a threshold.

In one example, the noise reduction circuit is further configured to provide a test driver signal to the speaker and the profile selection routine is further configured to compare the feedback audio signal with the test driver signal to identify acoustic characteristics of the subject. In this example, the test driver signal may include, for example, one of a chime, a tone, or a noise.

In one example, the ANR headphone further includes a user interface coupled to the processor wherein the processor is further configured to provide an indication of the selected profile via the user interface.

In one example, the ANR headphone further includes an interface to receive an audio signal from an external entity and wherein the controller information includes information indicative of a relationship between at least the feedback audio signal, the audio signal, and the driver signal. In this example, the noise reduction circuit may be further configured to generate the driver signal based on at least the controller information of the selected profile, the audio signal, and the feedback audio signal and provide the driver signal to the speaker.

In one example, the noise reduction circuit comprises a specialized integrated circuit. In one example, the noise reduction circuit is implemented within the processor according to software executed by the processor. In one example, the ANR headphone further includes a feed-forward microphone and an earpiece and wherein the feedback microphone and the speaker are disposed within the earpiece and wherein the feed-forward microphone is disposed on an external portion of the earpiece.

According to one aspect, an ANR headphone is provided. The ANR headphone includes a speaker to receive a driver signal and generate sound based on the driver signal, a feedback microphone to detect sound proximate the speaker and generate a feedback audio signal, a memory to store a plurality of profiles, each profile including controller information, a noise reduction circuit coupled to the speaker and the feedback microphone, a processor coupled to the noise reduction circuit and the memory, and a profile selection routine executable by the processor. The profile selection routine may be configured to select a profile from the plurality of profiles, provide the controller information of the selected profile to the noise reduction circuit. The noise reduction circuit may be configured to generate the driver signal based on at least the controller information of the selected profile and the feedback audio signal, and provide the driver signal to the speaker.

In one example, the ANR headphone further includes a user interface coupled to the processor to receive input from an external entity and wherein the profile selection routine is configured to select the profile based on the input from the external entity.

In one example, the plurality of profiles includes a default profile and wherein the profile selection routine is further configured to monitor a stability of the driver signal and select the default profile responsive to the driver signal being unstable.

According to one aspect, a method of canceling noise for an ANR headphone is provided. The method includes receiving a feedback audio signal representative of sound inside the ANR headphone from a feedback microphone, identifying acoustic characteristics of a subject wearing the ANR headphone, comparing the acoustic characteristics of the subject with the acoustic parameters, selecting a profile from a plurality of stored profiles, each profile including controller information and acoustic parameters, based on the comparison between the acoustic characteristics of the subject and the acoustic parameters of the selected profile, generating a driver signal based on at least the controller information of the selected profile and the feedback audio signal, and providing the driver signal to a speaker in the headphone.

In one example, the act of selecting the profile includes determining whether the acoustic characteristics of the subject match the acoustic parameters of the selected profile.

Still other aspects, examples, and advantages of these exemplary aspects are discussed in detail below. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

Furthermore, in the event of inconsistent usages of terms between this document and documents incorporated herein by reference, the term usage in the incorporated references is supplementary to that of this document; the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

DETAILED DESCRIPTION

The following examples describe systems and methods of active noise reduction (ANR) in headphones that improve noise reduction performance by employing more aggressive noise canceling techniques tailored to the acoustic information of the subject's ear canal. For instance, some examples disclosed herein manifest an appreciation that the acoustic characteristics of the ear canal vary between individuals, and noise reduction performance can be improved by tailoring the controller generating the noise canceling signals to the specific acoustic characteristics of the subject's ear canal. These customized controllers, however, may become unstable if the ear canal acoustics change (e.g., a different subject puts on the ANR headset). Accordingly, some examples include headphones capable of identifying the acoustic characteristics of the subject and switching between one or more customized controllers based on the identified acoustic characteristics of the current subject. Thereby, noise reduction performance may be improved without sacrificing user compatibility.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Example Active Noise Reduction Headphone

Figure 1:
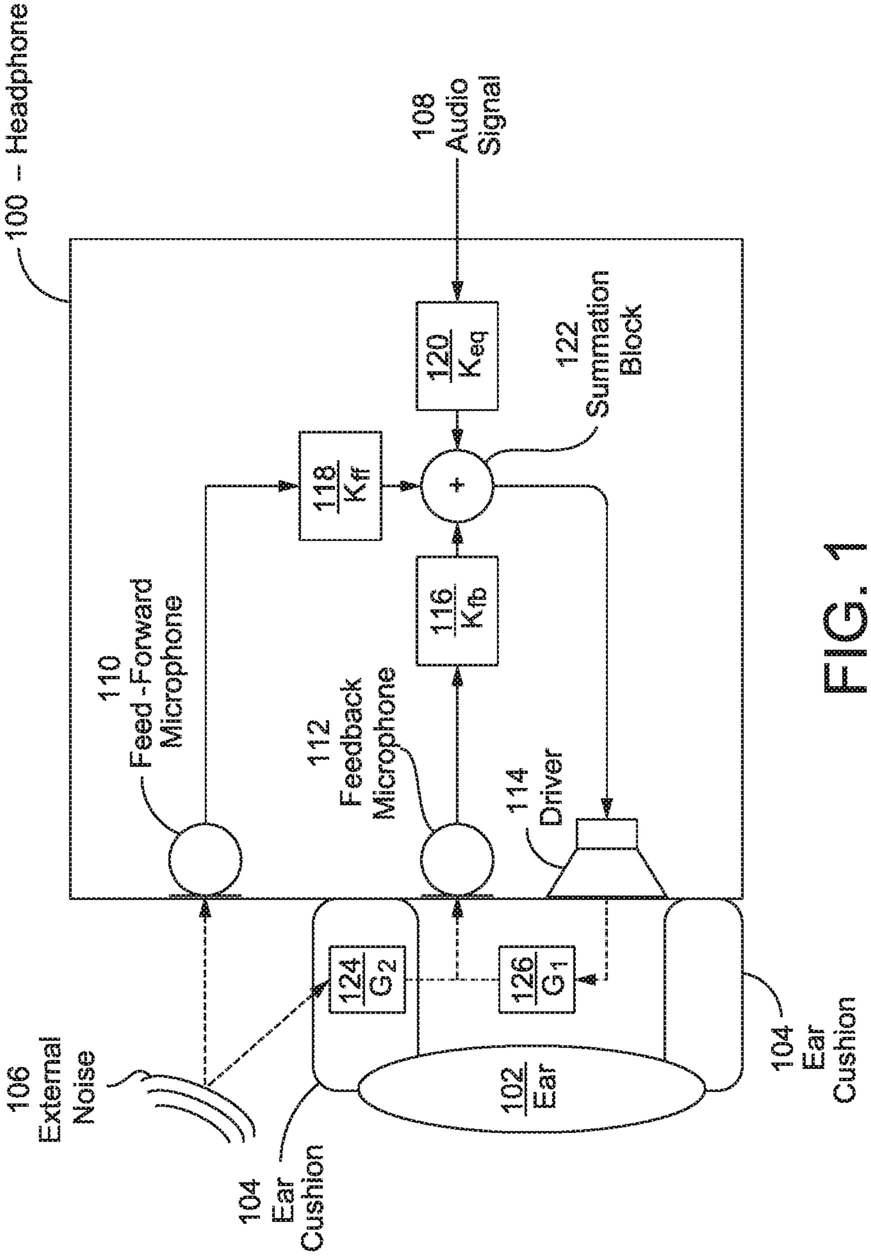
FIG. 1 is an illustration of an example ANR headphone.

Various examples disclosed herein implement customized controllers in ANR headphones. FIG. 1 illustrates an example ANR headphone 100 providing noise-canceled sound to an ear 102 of the subject based on a received audio signal 108 and the external noise 106. As shown, the headphone 100 includes ear cushions 104, a feed-forward microphone 110, a feedback microphone 112, and a driver 114. The headphone 100 generates a driver signal for the driver 114 based on the output of a feedback controller IQ, 116, a feed-forward controller $K_{ff}$ 118, and an audio controller $K_{eq}$ 120. It is appreciated that alternative arrangements of the controllers 116 and 118 and summation block 122 may also be used.

In some examples, the ear cushions 104 in combination with the structure of the headphone 100 (e.g., an earcup) may provide at least some degree of passive noise reduction (PNR) by isolating the ear 102 and feedback microphone 112 from the external noise 106. The impact of the PNR on the external noise 106 as the external noise 106 travels to the ear 102 and feedback microphone 112 is illustrated by the plant $G_2$ 124. The external noise that reaches the ear 102 and feedback microphone 112 may be canceled by sound from the driver 114 that destructively interferes with the noise.

The headphone 100, as illustrated, employs both feed-forward and feedback control techniques to generate the noise canceling signal. The feedback control loop may comprise the feedback microphone 112, the feedback controller $K_{fb}$ 116, and the driver 114. In the feedback control loop, the plant being controlled may be the sound proximate the ear canal of the subject illustrated as plant $G_1$ 126. The feedback microphone 112 acts as a sensor to observe the plant response based on the stimulus applied by the driver 114. Accordingly, the feedback controller $K_{fb}$ 116 may be designed to generate an appropriate driver signal for the driver 114 based on the sound detected by the feedback microphone 112.

Employing a feed-forward control path in combination with the previously described feedback control loop may improve the performance of the headphone 100 by enabling the headphone 100 to take preemptive action to cancel the external noise 106 that will soon reach the ear 102. The feed-forward control path may comprise the feed-forward microphone 110, the feed-forward controller $K_{ff}$ 118, and the driver 114. In the feed-forward control path, the feed-forward microphone 110 detects disturbances (e.g., the external noise 106) that will reach the ear 102 and the feed-forward controller $K_{ff}$ 118 generates a control signal for the driver 114 to adjust for the upcoming disturbance. The feed-forward control path may be employed in combination with the feedback control loop by, for example, summing the control signals as illustrated by the summation block 122. It is appreciated that an audio signal 108 and/or a filtered audio signal provided by the audio controller $K_{eq}$ 120 may be further combined with the control signals to both actively cancel the external noise 106 and play the audio signal 108 to the subject.

In some examples, the headphone 100 stores one or more customized controllers (e.g., feedback, feed-forward, and/or audio controllers) that are customized for the acoustic characteristics of the ear 102 of the subject. Employing customized controllers offers improved performance relative to generic controllers suitable for the general populace. The generic controllers need to be stable across a wide variety of ear canal acoustic characteristics and, consequently, generally offer sub-optimal performance for any particular subject. For example, the generic controller may be generated based on worst case plants $G_1$ 126 and/or $G_2$ 124, across all subjects. Customizing the controller for the subject eliminates the constraint that the controller must be stable across a variety of ear canal acoustic responses and, thereby, enables the design of controllers with better performance. In one example for illustration only, the controller gain may be customized for a subject while still meeting a gain margin constraint for stability. With customization, the controller gain could be increased on some subjects, leading to higher performance, while still meeting the required gain margin constraint for stability. It is appreciated that this example is a simplified case and other types of customized controller design approaches and/or customized controllers may be used.

The customized controllers, however, may become unstable if there is a change of the acoustic characteristics of the ear (e.g., the plant in the control loops) caused by, for example, another subject using the headphone. Accordingly, in some examples, acoustic parameters that identify the set of acoustic characteristics for which the controller is optimized may be stored together with the controller information as a profile. In these examples, the headphone may identify various acoustic characteristics of the current subject and compare the identified acoustic characteristics to the acoustic parameters of the profile to determine whether the particular controller design is compatible with the current subject. The headphone may store any number of profiles and switch between profiles as the acoustic characteristics of the subject change. Thereby, the headphone 100 may employ customized aggressive controllers offering improved performance while still being compatible with a wide range of ear canal acoustic characteristics.

Various methods may be employed to initially generate customized feedback and/or feed-forward controllers given knowledge of the plant and a desired plant response as is appreciated by a person of ordinary skill in the art given the benefit of this disclosure. For example, the controllers may be designed manually by fitting the device to a given user and adjusting the parameters to find the maximum gain achievable without instability. An automated process may employ modified devices that provide information to an automated system to play test tones, measure responses, and detect instability while adjusting parameters. The specifics of how the custom profile is created are beyond the scope of this disclosure. The completed profile including the customized controller may be received by the headphone via, for example, a communication interface and stored locally in the headphone. It is appreciated that components other than the feed-forward microphone 110, the feedback microphone 112, and/or the driver 114 shown in FIG. 1 may be employed to design and/or select a customized controller. For example, the headphone 100 may include a probe microphone (not illustrated) that may be inserted deep into the ear canal to measure in-canal pressure to design the customized controller.

In some examples, the customized controllers may have a customized frequency response. Employing a controller with a customized frequency response may be advantageous relative to other methods employing only a customized gain because it allows a greater degree of freedom to design the controller for a particular system. For example, a gain-only adjustment may only provide a fraction of the improvement relative to a generic controller that is possible with a customized frequency response. The customized frequency response may control gain as a function of frequency, or may include a more complex customized frequency response, i.e., controlling phase as well as gain as a function of frequency.

In at least one example, the customized controllers may be constructed to not completely cancel a subset of the external noise 106 to provide natural hear-through of select ambient sounds (e.g., human speech). Thereby, the headphone may cancel unwanted noise while still providing the subject situational awareness. Example modified controllers to provide natural hear-through of select sounds are described in U.S. Pat. No. 8,798,283, titled "PROVIDING AMBIENT NATURALNESS IN ANR HEADPHONES," issued on Aug. 5, 2014, and U.S. patent application Ser. No. 14/225,814, titled "COLLABORATIVELY PROCESSING AUDIO BETWEEN HEADSET AND SOURCE," filed on Mar. 26, 2014, each of which is hereby incorporated herein by reference in its entirety.

The headphone 100 has a variety of potential implementations. In at least some examples, the headphone 100 may be constructed as a headset. One such headphone implementation is the ANR headset 200 illustrated in FIG. 2. The ANR headset 200 includes earcups 202 connected by a headband 204. As illustrated, each earcup 202 includes an ear cushion 104, a feed-forward microphone 110, a feedback microphone 112, and a driver 114. It is appreciated that the ANR headset may further include a processor (not illustrated) to implement the controllers 116, 118, and 120 in addition to summation block 122 and/or a power source (not illustrated) to provide power to the processor.

Figure 2:
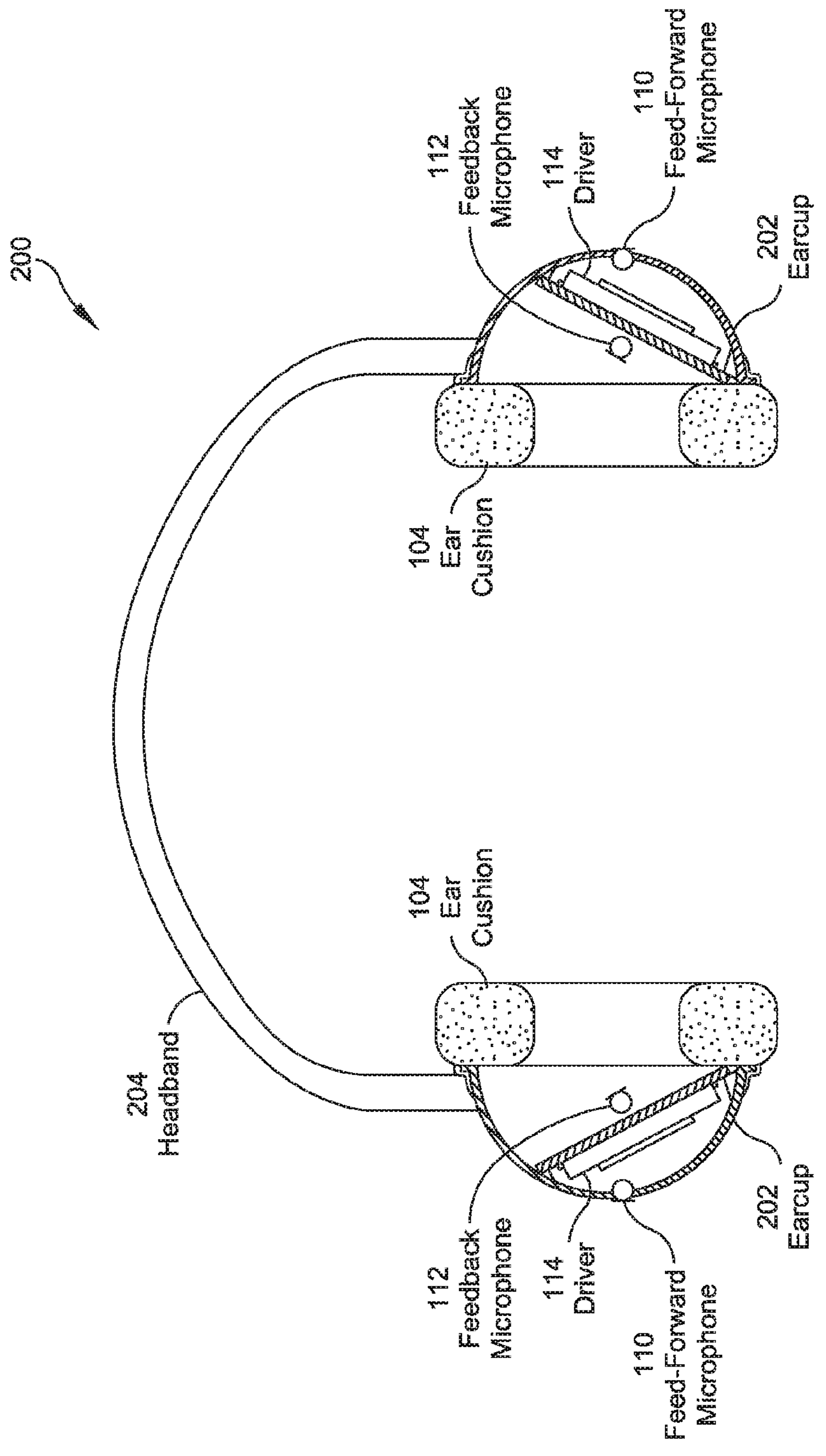
FIG. 2 is another illustration of an example ANR headphone.

As illustrated in FIG. 2, the feed-forward microphone 110 is disposed on an external portion of the earcup 202 to detect external noise and the feedback microphone 112 is disposed in the earcup proximate the driver 114. It is appreciated that other arrangements of the feed-forward microphone 110, the feedback microphone 112, and the driver 114 may be employed based on the particular application. In addition, the shape and size of the earcup 202 may be altered based on the desired design. For example, a smaller earcup 202 may be employed in on-ear headset implementations as opposed to over-ear headset implementations.

The construction of the ANR headset 200 may be altered based on the particular implementation. For example, the ANR headset 200 may be constructed as a mono headset and employ only one earcup 202 attached to the headband 204. In addition, the mono headset may further include a boom microphone to detect the speech of the subject. Accordingly, the ANR headset 200 is not limited to any particular implementation.

Figure 3A:
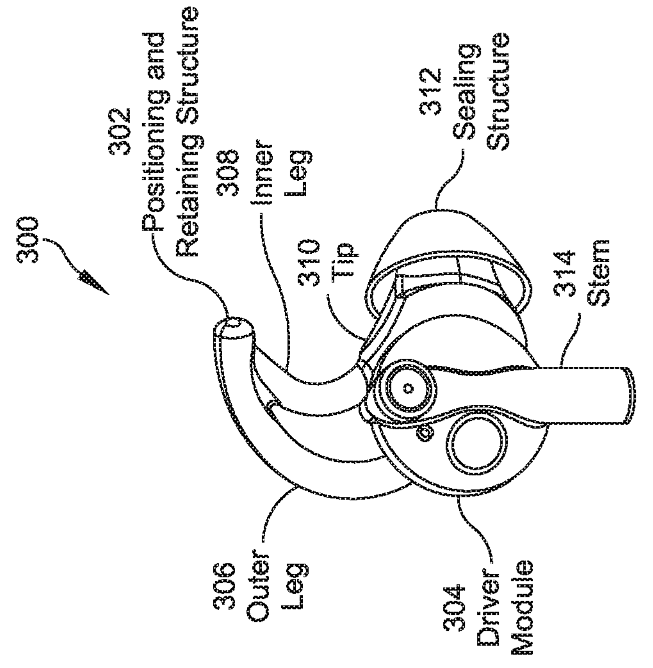
FIGS. 3A and 3B are another illustration of an example ANR headphone.
Figure 3B:
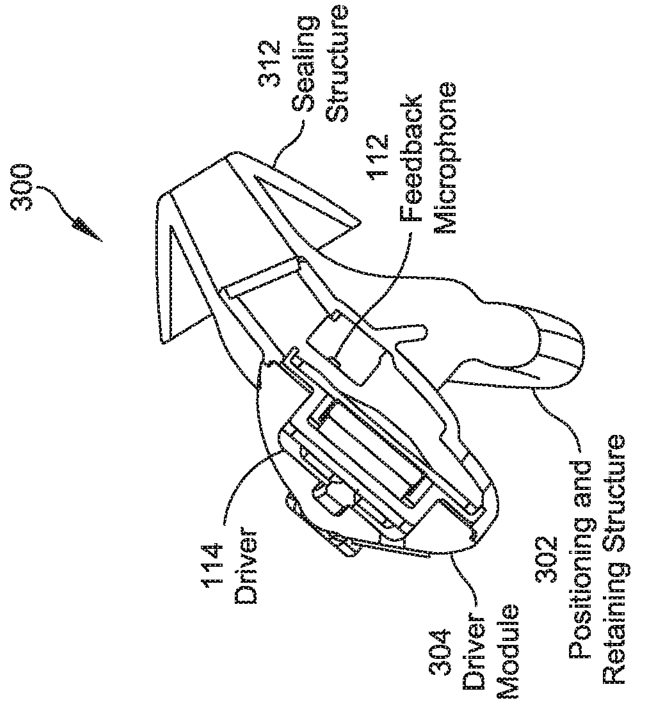

In another example, the headphone may be constructed as an in-ear ANR headset as illustrated in FIGS. 3A and 3B. FIG. 3A illustrates an external view of the in-ear ANR headset 300 including a positing and retaining structure 302, a driver module 304, a tip 310, a sealing structure 312, and a stem 314. Referring to FIG. 3B, a cross-sectional view of the in-ear ANR headset 300 is illustrated including a driver 114 and a feedback microphone 112 within the driver module 304. It is appreciated that the in-ear ANR headset 300 may further include various other electronic devices (not shown) including, for example, a feed-forward microphone and/or communication circuitry to wirelessly communication with an external device.

As illustrated in FIG. 3A, the positioning and retaining structure 302 includes an outer leg 306 and an inner leg 308 extending from the driver module 304. The outer leg 308 may be curved to generally follow the curve of the anti-helix wall at the rear of the concha of the subject's ear. A suitable positioning and retaining structure is described in U.S. Pat. No. 8,249,287, titled "EARPIECE POSITIONING AND RETAINING," issued on Aug. 21, 2012, which is hereby incorporated herein by reference in its entirety.

The sealing structure 312 seals the ear canal of the subject from external noise to provide passive noise reduction to the subject. The sealing structure 312 may include a conformable frusta-conically shaped structure that deflects inwardly when the in-ear ANR headset is urged into the ear canal of the subject. The frusta-conically shaped structure conforms with the features of the external ear at the transition region between the bowl of the concha and the ear canal. A suitable sealing structure is described in U.S. Pat. No. 8,737,669, titled "EARPIECE PASSIVE NOISE ATTENUATING," issued on May 27, 2014, which is hereby incorporated herein by references in its entirety.

In at least one example, the sealing structure 312 in combination with the positioning and retaining structure 302 may provide mechanical stability to the in-ear ANR headset 300. Accordingly, in some examples, no headband or other device is required to exert inward pressure in order to hold the in-ear ANR headset 300. Additional in-ear ANR headset configurations are described in U.S. Pat. No. 9,082,388, titled "IN-EAR ACTIVE NOISE REDUCTION EARPHONE," issued on Jul. 14, 2015, which is hereby incorporated herein by references in its entirety.

Figure 4:
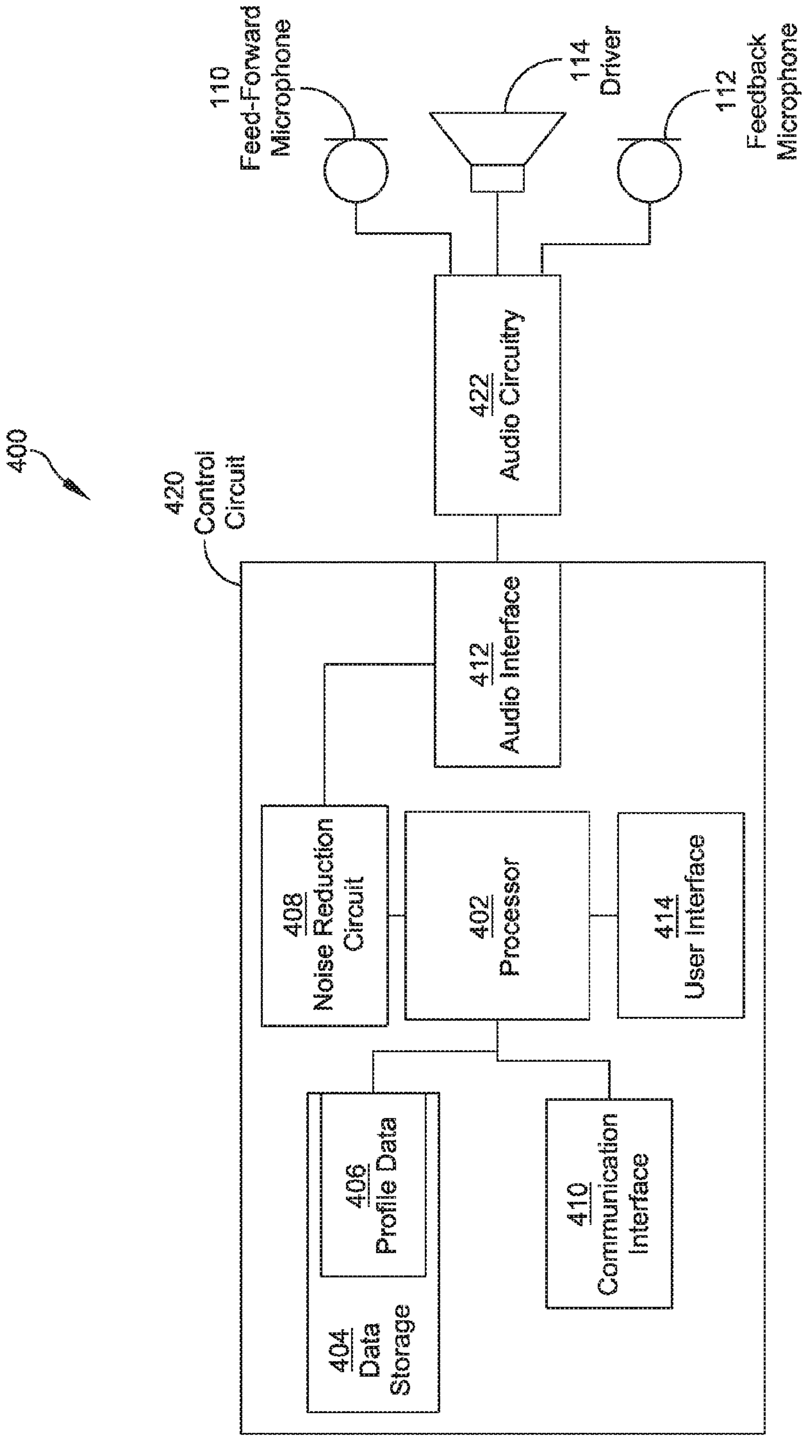
FIG. 4 is a functional schematic of one example ANR headphone.

The headphone may include additional components to facilitate the generation of the noise cancelling signals as illustrated by the functional schematic of example headphone 400 in FIG. 4. The headphone 400 includes a control circuit 420 in communication with a feed-forward microphone 110, a feedback microphone 112, and a driver 114 via audio circuitry 422. As illustrated, the control circuit 420 includes a processor 402, data storage 404 including profile data 406, a noise reduction circuit 408, a communication interface 410, an audio interface 412, and a user interface 414. It is appreciated that the headphone 400 may further include a rechargeable battery (not illustrated) and/or a receptacle to hold one or more disposable batteries (not illustrated) that provide electrical power to the other various components.

As illustrated in FIG. 4, the processor 402 is coupled to the data storage 404 and various interfaces 410, 412, and 414. The processor 402 performs a series of instructions that result in data which are stored in and retrieved from the data storage 404. The data storage 404 includes a computer readable and writeable nonvolatile data storage medium configured to store non-transitory instructions and data. The medium may, for example, be optical disk, magnetic disk or flash memory, among others, and may be permanently affixed to, or removable from, the headphone 400.

In some examples, the noise reduction circuit 408 is configured to actively cancel external noise by generating noise canceling signals. Example processes performed by the noise reduction circuit 408 are described in more detail below with reference to the Example Noise Reduction Processes section and FIGS. 5-10. The noise reduction circuit 408 may be implemented using hardware or a combination of hardware and software. For instance, in one example, the noise reduction circuit 408 is implemented as a software component that is stored within the data storage 404 and executed by the processor 402. In other examples, noise reduction circuit 408 may be an application-specific integrated circuit (ASIC) that is coupled to the processor 402. Thus, examples of the noise reduction circuit 408 are not limited to a particular hardware or software implementation.

In some examples, the profile data 406 includes data used by the noise reduction circuit 408 to generate noise canceling signals. For example, the profile data 406 may comprise one or more profiles including controller information and/or acoustic parameters for which the controller information is optimized. In addition, the profiles may also include a name or other identifier associated for the particular subject that the controller is optimized. As illustrated in FIG. 4, the noise reduction circuit 408 and the profile data 406 are separate components. However, in other examples, the noise reduction circuit 408 and the profile data 406 may be combined into a single component or re-organized so that a portion of the data are included in the noise reduction circuit 408. Such variations in these and the other components illustrated in FIG. 4 are intended to be within the scope of the examples disclosed herein.

As shown in FIG. 4, the headphone control circuit 420 includes several system interface components 410, 412, and 414. Each of these system interface components is configured to exchange, e.g., send or receive, data with one or more specialized devices that may be located within the headphone 400 or elsewhere. These specialized devices may include, for example, buttons, switches, light emitting diodes (LED), microphones, speakers, and/or antennas. The components used by the interfaces 410, 412, and 414 may include hardware components, software components or a combination of both.

In some examples, the components of the audio interface 412 couple one or more audio transducers including, for example, the feed-forward microphone 110, the feedback microphone 112, and the driver 114 to the noise reduction circuit 408 by providing, for example, analog-to-digital conversion and digital-to-analog conversion. The noise reduction circuit generates an output audio signal based on parameters loaded into it by the processor 402 or directly from the data storage 404. In some examples, the audio interface 412 provides the audio output signal generated by the noise reduction circuit 408 to the driver 114 via audio circuitry 422. The audio circuitry 422 may include, for example, various amplifiers and filters to condition the audio signals provided by and/or received from the audio interface 412. In some examples, the functionality of the audio circuitry 422 is incorporated into the audio interface 412 and the feed-forward microphone 110, the feedback microphone 112, and the driver 114 are directly coupled to the audio interface 412. In some examples, the audio interface itself is further incorporated into the noise reduction circuit 408, with an integrated component providing input and output interfacing and amplification, and applying the noise reduction and equalization filters $K_{fb}$, $K_{ff}$, and $K_{eq}$.

In some examples, the components of the communication interface 410 couple the processor 402 to other devices. For example, the communication interface 410 may enable communication between the processor 402 of the headphone control circuit 420 and, for example, a cellular phone, a portable media player, a computer-enabled watch, and/or a personal computer. The communication interface 410 may support any of a variety of standard and protocols including, for example, BLUETOOTH® and/or IEEE 802.11. The headphone control circuit 420 may perform one or more pairing processes to, for example, initially establish a communication link as described in commonly-owned U.S. Patent Publication No. 2014/0256260, titled "WIRELESS DEVICE PAIRING," filed on Mar. 7, 2013, which is hereby incorporated herein by reference in its entirety.

The user interface 414 shown in FIG. 4 includes a combination of hardware and software components that allow the headphone 400 to communicate with an external entity, such as a user. These components may be configured to receive information from actions such as physical movement and/or verbal intonation. Examples of the components that may be employed within the user interface 414 include buttons, switches, light-emitting diodes, touch screens, displays, stored audio signals, voice recognition, or an application on a computer-enabled device in communication with the headphone 400. In some examples, the user interface 414 enables the user to select a particular profile. For example, the user interface 414 may include a display presenting a list of profiles that the user may navigate via one or more scroll buttons and/or a select button. Each profile may be identified by, for example, a name associated with the control scheme (e.g., "John Doe's Profile").

Thus, the various system interfaces allow the headphone control circuit 420 to interoperate with a wide variety of devices in various contexts. It is appreciated that various interfaces may be removed from the headphone control circuit 420 based on the particular construction and features of the headphone. In addition, particular components may be adjusted or added to suit the particular construction of headphone 400.

Example Noise Reduction Processes

Figure 5:
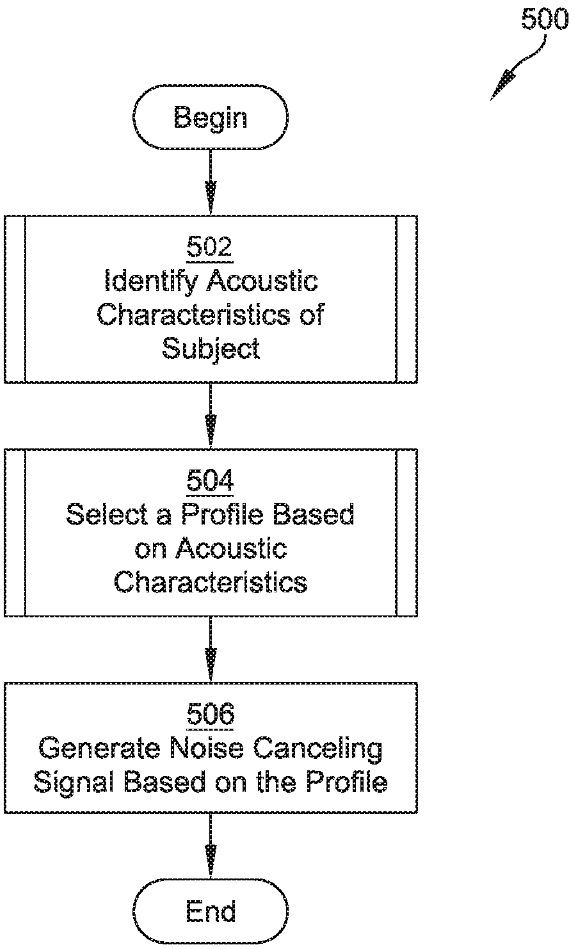
FIG. 5 is a flow diagram illustrating an example noise reduction process.
Figure 6:
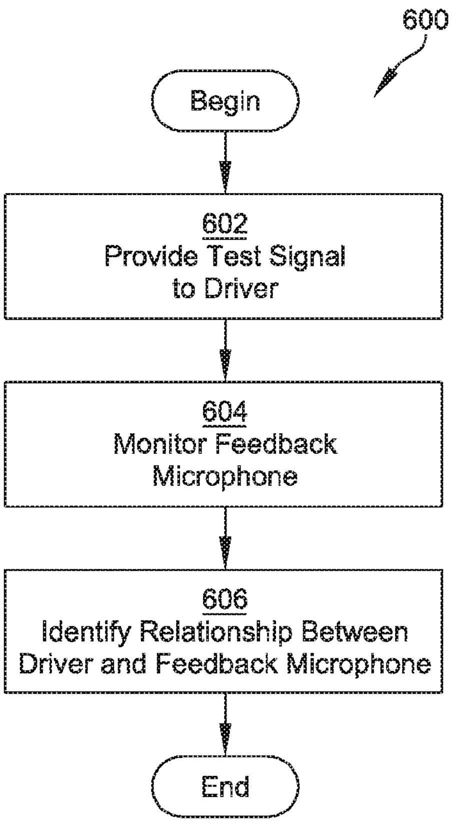
FIG. 6 is a flow diagram illustrating an example process to identify the acoustic characteristics of the subject.
Figure 7:
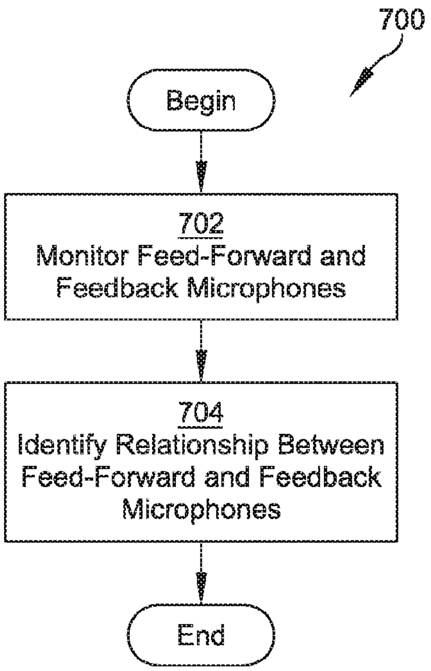
FIG. 7 is a flow diagram illustrating an example process to identify the acoustic characteristics of the subject.
Figure 8:
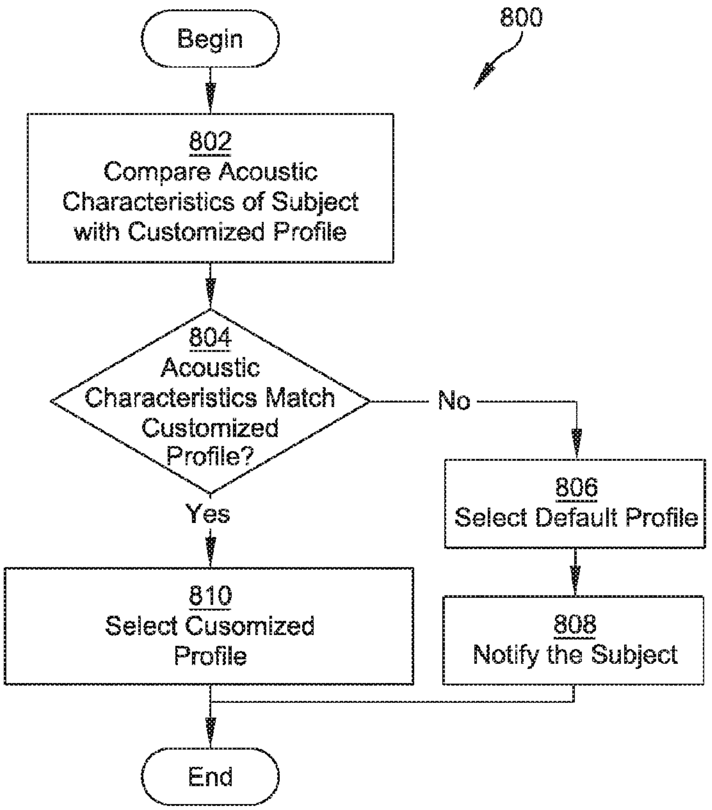
FIG. 8 is a flow diagram illustrating an example profile selection process.
Figure 9:
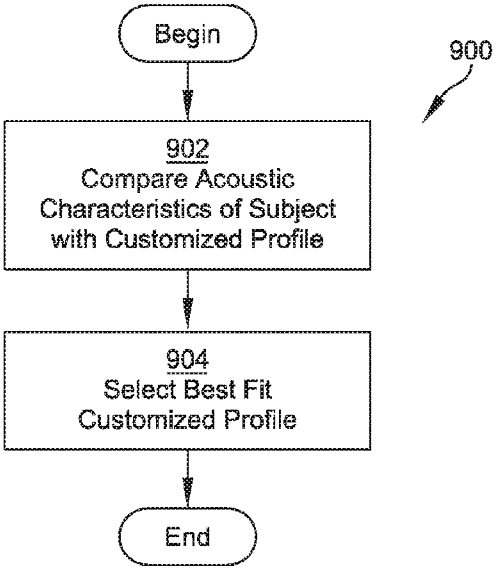
FIG. 9 is a flow diagram illustrating another example profile selection process.

Various examples implement and enable processes through which a headphone may provide active noise reduction. These processes may determine whether one or more aggressive controllers are suitable for the subject using the headphone based on the acoustic characteristics of the subject. FIG. 5 illustrates one such process 500 including an act 502 of identifying the acoustic characteristics of the subject, an act 504 of selecting a profile based on the acoustic characteristics of the subject, and an act 506 of generating a noise canceling signal based on the selected profile.

In act 502, the headphone identifies the acoustic characteristics of the subject using the headphone. For example, the headphone may identify the acoustic characteristics of the subject by identifying one or more relationships between the driver and one or more microphones. Referring back to FIG. 1, the headphone may identify one or more characteristics of the plant $G_1$ 126 and/or the plant $G_2$ 124. An example process to identify one or more characteristics of the plant $G_1$ 126 is described below with reference to FIG. 6 and an example process to identify one or more characteristics of the plant $G_2$ 124 is described below with reference to FIG. 7. It is appreciated that the headphone may determine one or more characteristics about the plant $G_1$ 126 and/or the plant $G_2$ 124.

In some examples, the headphone selects between determining the characteristics of plant $G_1$ 126 and determining the characteristics of plant $G_2$ 124 based on the particular environmental conditions. For example, identifying the characteristics of plant $G_2$ 124 using the process shown in FIG. 7 may be more accurate in the presence of loud external noise 106. Without sufficient external noise 106, the detected sound from the feed-forward microphone 110 and the feedback microphone 112 may primarily comprise noise from various electronic components, which is unrelated to the plant $G_2$ 124. Accordingly, the headphone may choose to determine the characteristics of plant $G_2$ 124 when the external noise 106 level is sufficiently above a threshold set to, for example, the noise floor of one or more electronic components within the headphone. The characteristics of plant $G_1$ 126, however, may be more difficult and/or less accurate to deduce from analyzing the sound detected by the feedback microphone 112 given stimulus from the driver 114 in high noise environments. Accordingly, the headphone may choose to determine the characteristics of plant $G_1$ 126 when the external noise 106 level is below a threshold level.

Referring back to FIG. 5, the headphone selects a profile based on the identified acoustic characteristics of the subject in act 504. Each profile may include, for example, a pre-built controller and/or a set of associated acoustic parameters for which the controller is optimized. The headphone may select a profile by comparing the identified acoustic characteristics of the subject with the acoustic parameters associated with various stored profiles. Example processes to select a profile are described below with references to FIGS. 8-10.

In act 506, the headphone generates the noise canceling signal based on the selected profile. For example, the headphone may load the controllers 116 and 118 associated with the selected profile and provide the generated control signal to the driver.

It is appreciated that the headphone may select an initial profile prior to performing acts 502, 504, and 506 in process 500. Selecting a profile immediately upon start-up of the headphone may advantageously minimize any perceived delay in providing noise-canceled sound to the user. For example, the headphone may employ a default profile suitable for a wide range of ear canals and subsequently perform process 500 to improve the noise reduction performance by employing a more suitable customized controller if appropriate. In another example, the headphone may initially select a customized controller suitable for a particular subject and monitor the stability of the control loop while performing process 500 to identify a more suitable aggressive controller if appropriate. For example, the headphone may select the most frequently used customized controller as the initial controller and switch to the default profile if the control loop becomes unstable caused by, for example, a mismatch between the acoustic characteristics of the subject and the acoustic parameters for which the controller was designed.

In some examples, the headphone identifies characteristics of the subject by identifying one or more characteristics of the plant $G_1$ 126 as illustrated in FIG. 1. The characteristics of the plant $G_1$ 126 may be identified by providing a known stimulus to the system via the driver 114 and analyzing the response of the system detected by the feedback microphone 112. One such process is illustrated by process 600 in FIG. 6. Process 600 includes an act 602 of providing a test signal to the driver, an act 604 of monitoring the feedback microphone, and an act 606 of identifying a relationship between the driver and the feedback microphone.

In act 602, the headphone provides a test signal to the driver. The test signal provides a known stimulus to the system to cause a system response that may be detected by the feedback microphone in act 604. Example test signals include various chimes, tones, and/or noises. The test signal may be stored locally in the memory of the headphone. It is appreciated that other signals may be used as the test signal. For example, the headphone may receive an audio signal from a handheld device and employ the received audio signal as the test signal. In another example, the headphone may employ a control signal generated by a loaded controller. For example, the headphone may load a generic controller suitable for a wide range of individuals and test signal may be the driver signal generated by the controller.

In act 606, the headphone identifies a relationship between the driver and the feedback microphone. For example, the headphone may identify a transfer function between the driver and the feedback microphone (e.g., transfer function $G_1$ 126). As is appreciated by a person of ordinary skill in the art given the benefit of this disclosure, various methods may be employed to identify a transfer function given a known stimulus and known response (e.g., blackbox system identification methods). In another example, the headphone may determine an approximation of the relationship between the driver and the feedback microphone to reduce the computational complexity. For example, the headphone may determine an energy ratio between the driver signal and the feedback microphone signal across a range of frequencies. The energy ratio may be determined by, for example, performing a Fast Fourier Transform (FFT) operation on the signals and determining a signal energy level at each frequency. The signal energy of the feedback microphone signal may be divided by the signal energy of the test signal at each frequency level to generate the energy ratio.

In some examples, the headphone identifies characteristics of the subject by identifying one or more characteristics of the plant $G_2$ 124 as illustrated in FIG. 1. The characteristics of the plant $G_2$ 124 may be identified by comparing the external noise 106 detected by the feed-forward microphone 110 with the filtered external noise 106 detected by the feedback microphone 112. One such process is illustrated by process 700 in FIG. 7. Process 700 includes an act 702 of monitoring the feed-forward and feedback microphones and an act 704 of identifying a relationship between the feed-forward and feedback microphones.

In act 702, the headphone monitors the sound detected by the feed-forward and feedback microphones. The sound detected by the feed-forward and feedback microphones may be analyzed to determine the relationship in act 704. As described above with reference to act 606 in FIG. 6, various methods may be employed to identifying the relationship between a measured stimulus (e.g., the external noise detected by the feed-forward microphone) and a measured response (e.g., the filtered noise detected by the feedback microphone). For example, an equivalent transfer function between the feed-forward and feedback microphone may be derived and/or the energy ratio between the feedback and feed-forward microphones may be determined.

In some examples, the headphone includes one or more customized profiles each tailored for a particular subject and/or subset of subjects providing improved performance relative to a default profile suitable for large proportion of the population. Accordingly, the headphone selects a profile by comparing the acoustic parameters of one or more customized profiles with the identified acoustic characteristics of the subject. One such process to select a profile is illustrated by process 800 in FIG. 8. Process 800 includes an act 802 of comparing the acoustic characteristics of the subject with the acoustic parameters of the customized profile, an act 804 of determining whether the identified acoustic characteristics match the acoustic parameters, an act 806 of selecting a default profile, an act 808 of notifying the subject, and an act 810 of selecting the customized profile.

Figure 10:
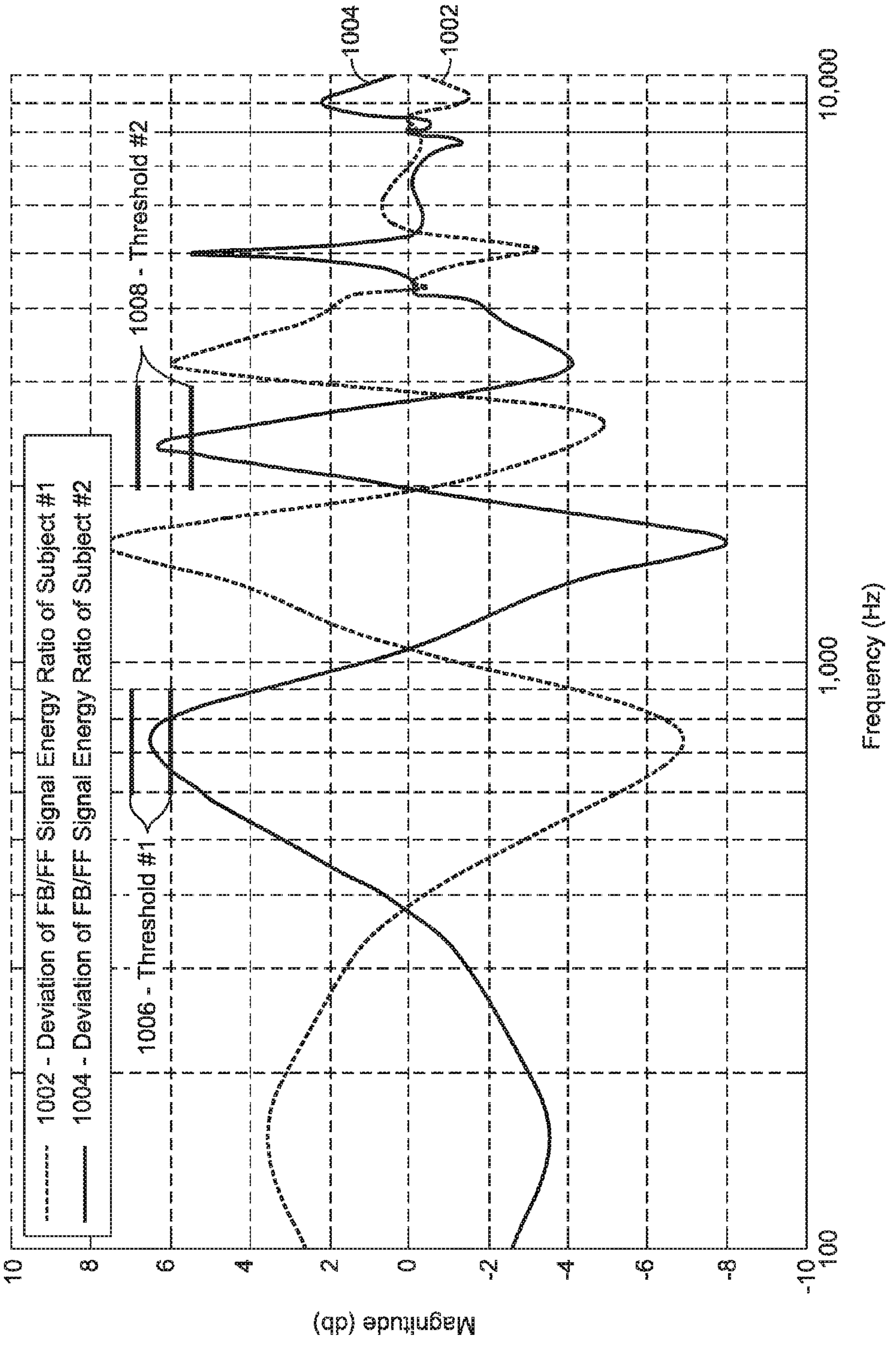
FIG. 10 is an example graph illustrating the deviation of the feedback (FB) to feed-forward (FF) signal energy ratio as compared to the energy ratio for a default feedback controller on reference subjects.

In act 802, the headphone compares the acoustic characteristics of the subject with the acoustic parameters associated with a customized profile. As previously described, the acoustic characteristics of the subject may be identified by energy ratios between the feedback microphone and the feed-forward microphone and/or between the feedback microphone and the driver. In these examples, acoustic parameters of each profile may include threshold energy ratios at particular frequencies to be compared against the identified energy ratio associated with the subject. Referring to FIG. 10, an example graph 1000 of the deviation of the feedback (FB) to feed-forward (FF) signal energy ratio as compared to the energy ratio for default feedback controller on a reference subject is illustrated for a first subject 1002 and a second subject 1004. As illustrated in FIG. 10, the deviation of the energy ratios of the first subject 1002 and the second subject 1004 have a near zero decibel average across the entire range from 100 Hz to 10 kHz. The energy ratio deviations, however, peak within particular frequency ranges. In some examples, the acoustic parameters associated with a profile may be stored as thresholds at particular frequency ranges as illustrated by a first threshold 1006 between 600 Hz and 900 Hz and a second threshold 1008 between 2000 Hz and 3000 Hz. The thresholds may be set at frequencies that generally have more deviation across subjects. Referring back to FIG. 8, the headphone determines whether the acoustic characteristics of the customized profile match the acoustic characteristics of the customized profile in act 804. For example, the headphone may determine that the identified energy ratio deviation associated with the subject is within a threshold specified by the acoustic parameters of the customized profile. If the headphone determines that the acoustic characteristics match the customized profile, the headphone proceeds to act 810 and selects the customized profile. Otherwise, the headphone proceeds to act 806 and selects the default profile.

In act 808, the headphone notifies the subject that the default profile is selected. The headphone may make the notification via a user interface of the headphone. For example, the headphone may illuminate one or more LED's on the headphone and/or present a notification to the user via a display. In another example, the headphone may play a pre-recorded message to notify the subject that the headphone is operating with a default controller. In addition, the headphone may notify the subject of the particular people for which the headphone has customized controllers stored. For example, the headphone may play a pre-recorded message stating "These headphones are customized for John Doe."

In some examples, the headphone includes a plurality of customized profiles each tailored for a particular subset of the population. As previously discussed, controllers designed to be stable across a large percentage of the human population sacrifice controller performance while controllers designed for a particular subject have better performance at the cost of user compatibility. The plurality of profiles may each be designed for a subset of the population with a particular set of similar acoustic characteristics and thereby reach a median between controller performance and user compatibility. For example, the acoustic characteristics of a variety of subjects may be measured and acoustic characteristics that are redundant may be removed to identify a set of acoustic characteristics to build the plurality of customized profiles. An example process to select the appropriate profile from the plurality of profiles is illustrated by process 900 in FIG. 9. Process 900 includes an act 902 of comparing the acoustic characteristics of the subject with the customized profiles and an act 904 of selecting the best fit customized profile.

In act 902, the headphone compares the acoustic characteristics of the subject with the acoustic parameters of the profile. Various methods may be employed to compare the acoustic parameters of the subject with the acoustic parameters of the profile as previously described with reference to act 802 in FIG. 8. In at least one example, the headphone employs a look-up table to simultaneously compare the acoustic characteristics of the subject with the acoustic parameters of the plurality of profiles. The look-up table may be created based on stored responses between, for example, the driver 114 and the feedback microphone 112 and/or parameterized versions of the plant $G_1$ 126. The look-up table may provide an indication of the customized profile with the best fit that may be selected in act 904.

In some examples, the headphone may adjust one or more parameters of the customized profile selected in act 904 to improve performance and/or stability. For example, the look-up table may identify a customized controller with a corresponding plant having the closest frequency response to the frequency response of the plant $G_1$ 126 and/or the plant $G_2$124. In this example, the headphone may compare the magnitude of the frequency response of the plant associated with the customized profile to the magnitude of the frequency response of the plant $G_1$ 126 and/or the plant $G_2$124 to identify a magnitude gap, if any. The headphone may then adjust the customized controller gains consistent with the identified magnitude gap between the frequency responses. It is appreciated that the headphone may perform a final check to ensure that any remaining differences between the frequency responses of the plant $G_1$ 126 and/or the plant $G_2$124 and the plant associated with the customized controller (after magnitude adjustment) do not violate any stability constraints.

Each of the processes disclosed herein depicts one particular sequence of acts in a particular example. The acts included in each of these processes may be performed by, or using, a headphone specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a headphone configured according to the examples disclosed herein.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. An active noise reduction (ANR) headphone comprising:
- a speaker to receive a driver signal and generate sound based on the driver signal;
- a feedback microphone to detect sound proximate the speaker and generate a feedback audio signal;
- a feed-forward microphone to detect ambient sound and generate a feed-forward audio signal;
- a memory to store a plurality of profiles, each profile including controller information, acoustic parameters, and at least one expected energy ratio between the feedback audio signal and the feed-forward audio signal and/or between the feedback audio signal and the driver signal;
- a noise reduction circuit coupled to the speaker and the feedback microphone;
- a processor coupled to the noise reduction circuit and the memory; and
- a profile selection routine executable by the processor and configured to:
  - determine at least one actual energy ratio between the feedback audio signal and the feed-forward audio signal and/or between the feedback audio signal and the driver signal to identify acoustic characteristics of a subject wearing the ANR headphone;
  - compare a difference between the at least one expected energy ratio and the at least one of the actual energy ratio with a threshold to compare the acoustic characteristics of the subject with the acoustic parameters of the plurality of profiles;
  - select a profile from the plurality of profiles based on the comparison between the acoustic characteristics of the subject with the acoustic parameters of the selected profile; and
  - provide the controller information of the selected profile to the noise reduction circuit.

2. The ANR headphone of claim 1, wherein the controller information includes information indicative of a relationship between at least the feedback audio signal and the driver signal.

3. The ANR headphone of claim 2, wherein the noise reduction circuit is configured to generate the driver signal based on at least the controller information of the selected profile and the feedback audio signal and provide the driver signal to the speaker.

4. The ANR headphone of claim 1, wherein the acoustic parameters in each profile include at least one of: a first energy ratio between the feedback audio signal and the feed-forward audio signal, a second energy ratio between the feedback audio signal and the driver signal, a first transfer function between the feedback audio signal and the feed-forward audio signal, or a second transfer function between the feedback audio signal and the driver signal.

5. The ANR headphone of claim 1, wherein the plurality of profiles includes a default profile and a customized profile and wherein the profile selection routine is further configured to determine whether the acoustic characteristics of the subject match the acoustic parameters of the customized profile.

6. The ANR headphone of claim 5, wherein the profile selection routine is further configured to select the profile at least in part by selecting the customized profile responsive to the acoustic characteristics of the subject matching the acoustic parameters of the customized profile.

7. The ANR headphone of claim 5, wherein the profile selection routine is further configured to select the profile at least in part by selecting the default profile responsive to the acoustic characteristics of the subject not matching the acoustic parameters of the customized profile.

8. The ANR headphone of claim 7, further comprising a user interface coupled to the processor and wherein the processor is further configured to provide an indication via the user interface that the default profile is selected.

9. The ANR headphone of claim 1, wherein the profile selection routine is further configured to select the profile with acoustic parameters that best fits the acoustic characteristics of the subject.

10. The ANR headphone of claim 1, wherein the memory further stores a look-up table associating acoustic characteristics of the subject with the plurality of profiles and wherein the profile selection routine is further configured to select the profile with acoustic parameters that best fits the acoustic characteristics of the subject by the look-up table.

11. The ANR headphone of claim 1, further comprising an interface to receive a customized profile from an external entity and wherein the processor is further configured to store the customized profile in the memory.

12. The ANR headphone of claim 1, wherein the noise reduction circuit is further configured to provide a test driver signal to the speaker and the profile selection routine is further configured to compare the feedback audio signal with the test driver signal to identify acoustic characteristics of the subject.

13. The ANR headphone of claim 12, wherein the test driver signal includes one of a chime, a tone, or a noise.

14. The ANR headphone of claim 1, further comprising a user interface coupled to the processor wherein the processor is further configured to provide an indication of the selected profile via the user interface.

15. The ANR headphone of claim 1, further comprising an interface to receive an audio signal from an external entity and wherein the controller information includes information indicative of a relationship between at least the feedback audio signal, the audio signal, and the driver signal.

16. The ANR headphone of claim 15, wherein the noise reduction circuit is further configured to generate the driver signal based on at least the controller information of the selected profile, the audio signal, and the feedback audio signal and provide the driver signal to the speaker.

17. The ANR headphone of claim 1, wherein the noise reduction circuit comprises a specialized integrated circuit.

18. The ANR headphone of claim 1, wherein the noise reduction circuit is implemented within the processor according to software executed by the processor.

19. The ANR headphone of claim 1, further comprising an earpiece and wherein the feedback microphone and the speaker are disposed within the earpiece and wherein the feed-forward microphone is disposed on an external portion of the earpiece.

20. An active noise reduction (ANR) headphone comprising:
- a speaker to receive a driver signal and generate sound based on the driver signal;
- a feedback microphone to detect sound proximate the speaker and generate a feedback audio signal;
- a feed-forward microphone to detect ambient sound and generate a feed-forward audio signal;
- a memory to store a plurality of profiles, each profile including controller information and at least one expected energy ratio between the feedback audio signal and the feed-forward audio signal and/or between the feedback audio signal and the driver signal;

a noise reduction circuit coupled to the speaker and the feedback microphone;

a processor coupled to the noise reduction circuit and the memory; and a profile selection routine executable by the processor and configured to:

determine at least one actual energy ratio between the feedback audio signal and the feed-forward audio signal and/or between the feedback audio signal and the driver signal;

compare a difference between the at least one expected energy ratio and the at least one of the actual energy ratio with a threshold;

select a profile from the plurality of profiles;

provide the controller information of the selected profile to the noise reduction circuit;

wherein the noise reduction circuit is configured to:

generate the driver signal based on at least the controller information of the selected profile and the feedback audio signal; and provide the driver signal to the speaker.

21. The ANR headphone of claim 20, further comprising a user interface coupled to the processor to receive input from an external entity and wherein the profile selection routine is configured to select the profile based on the input from the external entity.

22. The ANR headphone of claim 20, wherein the plurality of profiles includes a default profile and wherein the profile selection routine is further configured to monitor a stability of the driver signal and select the default profile responsive to the driver signal being unstable.

23. A method of canceling noise for an active noise canceling (ANR) headphone comprising:

receiving a feedback audio signal representative of sound inside the ANR headphone from a feedback microphone;

receiving a feed-forward audio signal representative of ambient sound from a feed-forward microphone;

identifying acoustic characteristics of a subject wearing the ANR headphone including determining at least one actual energy ratio between the feedback audio signal and the feed-forward audio signal and/or between the feedback audio signal and a driver signal;

comparing a difference between at least one expected energy ratio between the feedback audio signal and the feed-forward audio signal, and/or between the feedback audio signal and the driver signal, and the at least one of the actual energy ratio, with a threshold, to compare the acoustic characteristics of the subject with acoustic parameters;

selecting a profile from a plurality of stored profiles, each profile including controller information and the acoustic parameters, based on the comparison between the acoustic characteristics of the subject and the acoustic parameters of the selected profile;

generating the driver signal based on at least the controller information of the selected profile and the feedback audio signal; and providing the driver signal to a speaker in the headphone.

24. The method of claim 23, wherein selecting the profile includes determining whether the acoustic characteristics of the subject match the acoustic parameters of the selected profile.

* * * * *